United States Patent
Wang et al.

(10) Patent No.: US 9,765,014 B2
(45) Date of Patent: Sep. 19, 2017

(54) PROCESS FOR PRODUCING DIMETHYL CARBONATE

(71) Applicant: YASHENTECH CORPORATION, Shanghai (CN)

(72) Inventors: Youqi Wang, Shanghai (CN); Xunwen Wang, Shanghai (CN); Zhijian Li, Shanghai (CN); Hui Han, Shanghai (CN)

(73) Assignee: YASHENTECH CORPORATION, Zhangjiang Hitech Park, Pudong, Shanghai (CN)

( * ) Notice: Subject to any disclaimer, the term of this patent is extended or adjusted under 35 U.S.C. 154(b) by 0 days.

(21) Appl. No.: 14/863,328

(22) Filed: Sep. 23, 2015

(65) Prior Publication Data

US 2017/0057904 A1    Mar. 2, 2017

(30) Foreign Application Priority Data

Aug. 31, 2015   (CN) .......................... 2015 1 0546179

(51) Int. Cl.
| | |
|---|---|
| *C07C 68/06* | (2006.01) |
| *C07C 68/00* | (2006.01) |
| *C07C 68/08* | (2006.01) |
| *C07D 317/36* | (2006.01) |

(52) U.S. Cl.
CPC ............ *C07C 68/065* (2013.01); *C07C 68/00* (2013.01); *C07C 68/08* (2013.01); *C07D 317/36* (2013.01)

(58) Field of Classification Search
CPC .................................................. C07C 68/065
USPC ........................................................ 548/400
See application file for complete search history.

(56) References Cited

U.S. PATENT DOCUMENTS 5,489,702 A    2/1996  Doya et al.

FOREIGN PATENT DOCUMENTS

| CN | 1569810 A | 1/2005 |
|---|---|---|
| CN | 104557553 A1 | 4/2015 |
| EP | 0638541 A1 | 2/1995 |
| GB | 2280672 A | 2/1995 |
| JP | 1036322 A1 | 2/1998 |
| WO | 2009143785 A2 | 12/2009 |

OTHER PUBLICATIONS

International Search Report of PCT application No. PCT/CN/2015/088601 dated on May 27, 2016.
Written Opinion of the International Search Report of PCT application No. PCT/CN/2015/088601 dated on May 27, 2016.
Zhang, T. et al, "Zn-Mg mixed oxide as high-efficiency catalyst for the synthesis of propylene carbonate by urea alcoholysis", Catalysis Communications, Mar. 16, 2015, pp. 38-41, vol. 66.
Wang, P. et al., "Two-step synthesis of dimethyl carbonate from urea, ethylene glycol and methanol using acid-base bifunctional zinc-yttrium oxides", Fuel Processing Technology, Jun. 7, 2014, pp. 359-365, vol. 126, 2014.
Zhang, G. et al., "Preparation of Ca-Zn-Al Oxides and Their Catalytic Performance in the One-Pot Synthesis of Dimethyl Carbonate from Urea, 1, 2—Propylene Glycol, and Methanol", Industrial & Engineering Chemistry Research, Mar. 13, 2015, pp. 3515-3523, vol. 54, No. 13.
Bhanage, B.M. et al., "Transesterification of Urea and Ethylene Glycol to Ethylene Carbonate As an Important Step for Urea Based Dimethyl Carbonate Synthesis", Green Chemistry, Jun. 9, 2003, pp. 429-432, vol. 5, No. 4.
Fujita, S. -I. et al., "Chemical Fixation of Carbon Dioxide: Green Processes to Valuable Chemicals", Progress in Catalysis Research, 2005, pp. 57-79.

*Primary Examiner* — Kristin Vajda
(74) *Attorney, Agent, or Firm* — Jun He Law Office P.C.; James J. Zhu

(57) ABSTRACT

The present disclosure provides a process for producing dimethyl carbonate with high conversion rate. Alkylene glycol reacts with urea via alcohylysis reaction to produce alkylene carbonate and ammonia. The alkylene carbonate produced reacts with methanol via transesterification reaction to produce dimethyl carbonate. Before the dimethyl carbonate is separated from the mixture, the nitrogen-containing impurities are substantially removed. Unreacted feedstock and catalysts are recycled in the process.

20 Claims, 2 Drawing Sheets

PROCESS FOR PRODUCING DIMETHYL CARBONATE

CROSS-REFERENCE TO RELATED APPLICATIONS

This application claims priority to Chinese Patent Application No. 2015105461795, filed Aug. 31, 2015, the disclosure of which is incorporated herein by reference.

FIELD OF THE INVENTION

The present invention generally relates to the process for producing dimethyl carbonate.

BACKGROUND OF THE INVENTION

Dimethyl carbonate (DMC) is an important intermediate widely used in the chemical industry. Due to its low toxicity, DMC is considered a green reagent with many promising application prospects. At room temperature, DMC is a colorless, flammable liquid. It is mutually soluble with many organic solvents, such as alcohol, ester and ketones, and also having good hydrophobicity. Since DMC contains highly reactive functional groups, e.g., methyl, methoxy, carbonyl and methoxy carbonyl groups in its molecular structure, it is a versatile chemical and can be used as a better substitute for dimethyl sulphate, phosgene, or methyl halide, which are toxic and/or corrosive, in a variety of synthetic organic routes such as methylation, carbonylation, and transesterification, which meets the increasing demands for clean and green processes in the chemical industry.

DMC can also be used as a solvent to replace halogenated solvents. In addition, DMC has a high octane number and high oxygen content (53% wt), and as such can be used as a good additive to transportation fuels to reduce harmful emissions.

Currently, DMC can be produced on industrial scale via the following processes: 1) phosgene; 2) oxidative carbonylation of methanol; 3) transesterification; and 4) urea alcoholysis.

In phosgene route, DMC is produced from methanol and phosgene in concentrated NaOH solution. Because of the use of phosgene, which is highly toxic (chemical weapons reagent and potentially used as weapons of mass destruction) and corrosive, this process has been phased out in the industry.

Non-phosgene routes include oxidative carbonylation of methanol in liquid phase (see U.S. Pat. No. 4,318,862 to Romano et al.) and gas phase (see U.S. Pat. No. 5,162,563 to Nishihira et al.). Whether the process is carried out in liquid phase or gas phase, the main catalysts are metal chlorides, such as $CuCl_2$ or $CuCl$, which loses its activity rapidly. The deactivated catalyst reacts with water, which is a product of the oxidative carbonylation process, and forms hydrochloric acid. Hydrochloric acid is highly corrosive to reactor vessels, which results in high capital investment. The chloride ions in the product stream is difficult to remove, thus negatively impacts the quality of the final product. Additionally, the process operates at elevated pressures and other stringent conditions, making it economically less viable.

The transesterification route produces DMC by transesterification of cyclic carbonate (e.g., ethylene carbonate) with methanol (see U.S. Pat. No. 4,661,609 to Knifton, U.S. Pat. No. 4,691,041 to Duranleau et al.). The main disadvantage of the route includes cyclic carbonate, being an expensive chemical, is used as feedstock. Alternatively, cyclic carbonate may be obtained via epoxide reacting with $CO_2$. However, epoxide is also an expensive feedstock. The slow reaction rate of epoxide with $CO_2$, the need of high reaction pressure, and the thermal equilibrium limitation of the reaction further hamper such alternative. In addition, such process leads to the significant co-production of alkylene glycol, which puts constraints on the scale of DMC production.

The urea alcoholysis route, being based on inexpensive and renewable raw materials, is an attractive alternative. In this route, DMC is produced by reacting primary aliphatic alcohols such as methanol with urea in the presence of various heterogeneous and homogeneous catalysts such as dibutyl tin dimethoxide, tetraphenyl tin, etc (see, e.g., P. Ball et al, Synthesis of carbonates and polycarbonates by reaction of urea with hydroxyl compounds. C1 Mol. Chem. 1984, 1, 95). However, the route is not without limitations, such as low yield and high energy cost. Ryu et al. revealed the process of producing DMC from methanol and urea in a distillation tower (U.S. Pat. No. 5,902,894 to Ryu and U.S. Pat. No. 6,392,078 to Ryu et al.). Unfortunately, the conversion rate and selectivity are rather low due to catalysts and process conditions utilized. More recently, homogeneous and heterogeneous catalysts and catalytic distillation techniques are revealed in Chinese Patent Application Nos. CN1428329, CN1431190A, CN1569809A, CN1131660A. Due to the nature of the catalytic distillation process, the structure of the reactor is necessarily complex and the operating conditions are quite demanding. Consequently this process is difficult to be scaled up for industrial scale production of DMC.

Therefore, there is clear and continuing need for developing new processes to manufacture DMC.

BRIEF SUMMARY OF THE INVENTION

In an aspect, the present disclosure provides a process for producing dimethyl carbonate. In one embodiment, the process comprises the steps of: (a) reacting alkylene glycol and urea in the presence of an alcoholysis catalyst to produce alkylene carbonate and ammonia; (b) recovering at least a portion of the alkylene carbonate produced in step (a); (c) reacting the alkylene carbonate from step (b) and methanol in the presence of an transesterification catalyst to produce dimethyl carbonate and alkylene glycol; (d) recovering a mixture comprising the dimethyl carbonate and a first portion of unreacted methanol; and (e) separating the dimethyl carbonate from the mixture, wherein nitrogen-containing impurities are substantially removed in one or more steps of the process such that the mixture in separation step (e) is substantially free of nitrogen-containing impurity.

In certain embodiments, the nitrogen-containing impurity is substantially removed from the alkylene carbonate in recovery step (b). In certain other embodiments, the nitrogen-containing impurity is substantially removed from the mixture in reaction step (c).

In certain embodiments, the first portion of unreacted methanol is separated from the mixture and reused in step (c). In certain embodiments, nitrogen containing impurity is substantially removed from the first portion of unreacted methanol separated. In certain embodiments, the first portion of unreacted methanol is separated via a pressure varying azeotrope separation process. In certain embodiments, the first portion of unreacted methanol is separated via an extraction process. In certain embodiments, the extractant used in the extraction process is ortho-xylene.

In certain embodiments, the nitrogen-containing impurity is substantially removed via an acid resin.

In certain embodiments, at least a portion of the ammonia produced in reaction step (a) is recovered to react with $CO_2$ to produce urea. In certain embodiments, the ammonia recovered is further purified to remove substantially all organic impurities before reacting with $CO_2$ to produce urea.

In certain embodiments, at least a portion of the alcoholysis catalyst is recovered from the effluent from step (a) and reused in step (a).

In certain embodiments, unreacted alkylene glycol is recovered from the effluent from step (a) and reused in step (a).

In certain embodiments, unreacted methanol is recovered from the effluent from step (c) and reused in step (c).

In certain embodiments, at least a portion of the transesterification catalyst is recovered from the effluent from step (c) and reused in step (c).

In certain embodiments, the alkylene glycol is ethylene glycol or propylene glycol.

In certain embodiments, the alcoholysis catalyst is comprised of at least two metal oxides, wherein the metals are selected from the group consisting of copper, zinc, magnesium, aluminum, iron, zirconium, and titanium.

In certain embodiments, the alkylene glycol produced in reaction step (c) is recovered and reused in reaction step (a).

In certain embodiments, conversion percentage of urea is in the range of 95-100%.

In certain embodiments, conversion percentage of alkylene carbonate is in the range of 95-100%.

ABBREVIATION USED

DMC: dimethyl carbonate
PG: propylene glycol
PC: propylene carbonate

DETAILED DESCRIPTION OF THE INVENTION

Figure 1:
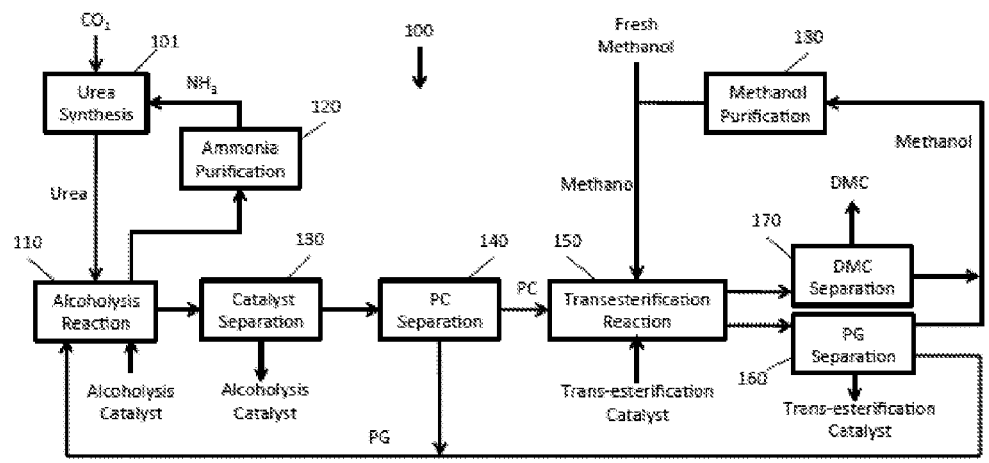
FIG. 1. A schematic illustrates the process for producing DMC.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

In an aspect, the present disclosure provides a process for producing dimethyl carbonate (DMC). In certain embodiments, the process comprises the steps of: (a) reacting alkylene glycol and urea in the presence of an alcoholysis catalyst to produce alkylene carbonate and ammonia; (b) recovering at least a portion of the alkylene carbonate produced in step (a) from an effluent from step (a); (c) reacting the alkylene carbonate from step (b) and methanol in the presence of an transesterification catalyst to produce dimethyl carbonate and alkylene glycol; (d) recovering a mixture comprising the dimethyl carbonate and a first portion of unreacted methanol; and (e) separating the dimethyl carbonate from the mixture, wherein nitrogen-containing impurities are substantially removed in one or more steps of the process such that the mixture in separation step (e) is substantially free of nitrogen-containing impurities.

As used herein, the term "nitrogen-containing impurities" refers to nitrogen compounds generated during a chemical reaction that involves urea. Examples of the nitrogen-containing impurities include, without limitation, ammonia, urea, biuret, polyurea, N-heterocyclic compounds, melamine, ammeline, ammelide, cyanuric acid, cyanic acid, isocyanic acid and cyamelide. Some examples of side reactions that generate nitrogen-containing impurities are represented by the following reaction schemes:

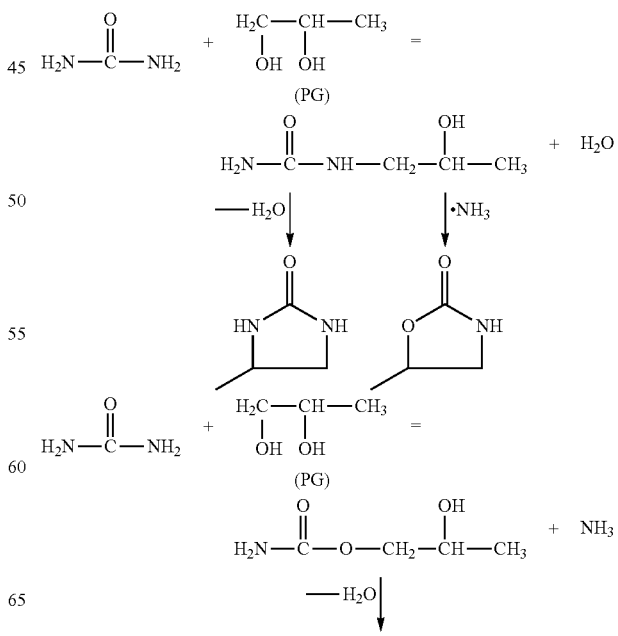

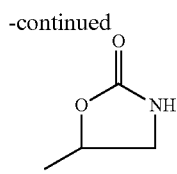

In certain embodiments, the major component of nitrogen-containing impurities is ammonia.

The present disclosure is based on the discovery that the nitrogen-containing impurities, e.g., ammonia, catalyze the decomposition of DMC, thus reducing the yield of DMC. For example, in the transesterification reaction, nitrogen contaminants in PC react with methanol to generate nitrogen-containing impurities, including ammonia, which is then present in the azeotrope of DMC and methanol. During the DMC separating step, the nitrogen-containing impurities in the azeotrope catalyze the decomposition of DMC. The process of the present disclosure removes the nitrogen-containing impurities in one or more steps of the process before the separating step such that the mixture in the DMC separating step is substantially free of nitrogen-containing impurity, thus increasing the yield of DMC.

In certain embodiments, the nitrogen-containing impurities are substantially removed from the alkylene carbonate before feeding the alkylene carbonate to the transesterification reaction. For example, the alkylene carbonate recovered from the alcoholysis catalyst separating device can be treated with an acid resin to substantially remove the nitrogen-containing impurities.

In certain embodiments, nitrogen-containing impurities are substantially removed from the mixture, e.g., azeotrope before the step of separating DMC from methanol. Suitable means to remove nitrogen-containing impurities are known in the art. For example, the DMC-containing effluent from the transesterification reaction can be treated with an acid resin or an acid molecular sieve (e.g., HY) or gamma-$Al_2O_3$ to substantially remove the nitrogen-containing impurities. In certain embodiments, the nitrogen-containing impurities are removed using an acid resin (e.g., DNW-1 (Mingzhu Special Type Resin Co. Ltd., Dandong, Liaoning) or D001 (Shengquan Chemical Ltd., Langfang, Hebei)).

In certain embodiments, unreacted methanol from the transesterification reaction is recovered and reused in the transesterification reaction. Before feeding the recovered methanol back to the transesterification reaction, nitrogen-containing impurities are substantially removed from the unreacted methanol.

As used herein, the term "nitrogen-containing impurities are substantially removed" or "substantially free of nitrogen-containing impurity" means that the concentration of the nitrogen-containing impurities in the mixture is at a level that at least 90%, preferably 95%, more preferably 99% of the DMC does not decompose during the DMC separation step. In certain embodiments, the concentration of the nitrogen-containing impurities in the mixture is lower than 1,000 ppm, lower than 900 ppm, lower than 800 ppm, lower than 700 ppm, lower than 600 ppm, lower than 500 ppm, lower than 400 ppm, lower than 300 ppm, lower than 200 ppm, lower than 100 ppm, lower than 90 ppm, lower than 80 ppm, lower than 70 ppm, lower than 60 ppm, lower than 50 ppm, lower than 40 ppm, lower than 30 ppm, lower than 20 ppm, lower than 10 ppm, lower than 9 ppm, lower than 8 ppm, lower than 7 ppm, lower than 6 ppm, lower than 5 ppm, lower than 4 ppm, lower than 3 ppm, lower than 2 ppm, lower than 1 ppm.

One of the discoveries of the current invention is that the nitrogen-containing impurities, e.g., ammonia, catalyze the decomposition of DMC during the DMC separating step, thus reducing the yield of DMC. By removing the nitrogen-containing impurities before the separation step, the process of the present disclosure unexpectedly increases the yield of DMC.

According to the process as disclosed herein, DMC can be produced from urea and methanol at high yield. In certain embodiments, conversion percentage of urea is more than 90%, 91%, 92%, 93%, 94%, 95%, 96%, 97%, 98%, and 99%. In certain embodiments, conversion percentage of urea is in the range of 95~100%. In certain embodiments, conversion percentage of alkylene carbonate is more than 90%, 91%, 92%, 93%, 94%, 95%, 96%, 97%, 98%, and 99%. In certain embodiments, conversion percentage of alkylene carbonate is in the range of 95~100%.

As used herein, the term "conversion rate" or "conversion percentage" means the percentage of starting material converted into the expected product.

One embodiment of the subject process is illustrated in FIG. 1. With reference to FIG. 1, this embodiment of the process 100 may involve reacting alkylene glycol and urea to produce alkylene carbonate, reacting the alkylene carbonate and methanol to produce DMC, and separating DMC from the reaction mixture. Nitrogen-containing impurities are produced during the process and are substantially removed in one or more steps of the process such that the mixture from which DMC is separated is substantially free of nitrogen-containing impurity.

As illustrated in FIG. 1, carbon dioxide and ammonia are fed into a urea synthesis device 101 to produce urea. The urea generated and PG are fed into an alcoholysis reactor 110 to produce PC and ammonia. The alcoholysis reaction can be represented by the following reaction scheme:

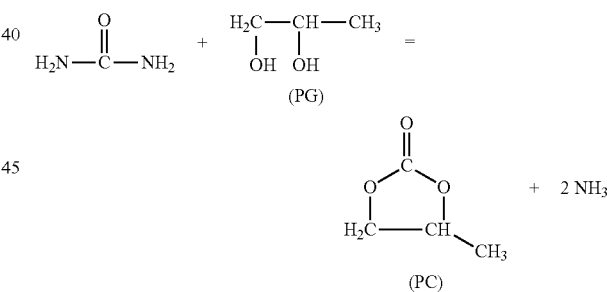

The ammonia produced can be recovered and treated via a purification device 120 to remove impurities. Purified ammonia can be used to react with $CO_2$ to produce urea, such as in device 101, thus forming recycled use of ammonia.

The effluent of the alcoholysis reaction contains PC, PG and alcoholysis catalyst. The effluent can be treated with a catalyst-separating device 130 to separate the alcoholysis catalyst.

The effluent of the alcoholysis reaction can further be treated with a PC-separating device 140 to separate the PC and PG. The PG separated can be reused in the alcoholysis reaction in the alcoholysis reactor 110.

The PC separated from the PC-separating device 140 is fed to a transesterification reactor 150 to react with methanol in the presence of a transesterification catalyst to produce DMC and PG. The transesterification reaction can be represented in the following reaction scheme:

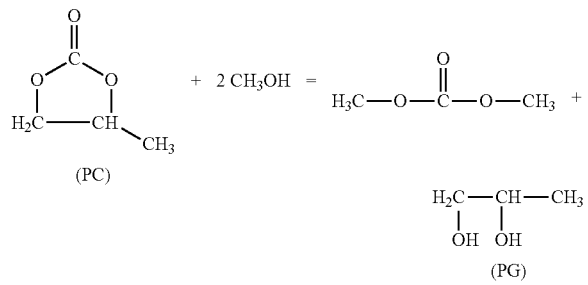

A first effluent of the transesterification reactor 150 contains unreacted methanol, PG produced in the transesterification reaction and transesterification catalyst. The first effluent can be treated with a PG-separating device 160 to separate the unreacted methanol, the PG and the transesterification catalyst. The unreacted methanol separated from the first effluent can be treated with a methanol-purification device 180 before being reused in the transesterification reaction. The PG separated from the first effluent can be reused in alcoholysis reaction. The transesterification catalyst separated from the first effluent can be reused in the transesterification reaction.

A second effluent of the transesterification reactor 150 contains DMC and unreacted methanol. The second effluent is treated with a DMC separating device 170 to separate DMC and unreacted methanol. The unreacted methanol separated from the second effluent can be treated with the methanol-purification device 180 before being reused in the transesterification reaction.

The preferred molar ratio of PG to urea in the alcoholysis reaction is around 1:1 to around 5:1, preferably around 1.5:1 to around 3:1. In certain embodiments, the alcoholysis catalyst is a solid complex catalyst comprises at least two metal oxides, wherein the metals are selected from the group consisting of copper, zinc, magnesium, aluminum, iron, zirconium, and titanium. In certain embodiments, the alcoholysis catalyst is present at around 0.1~5% (wt), preferably 0.3~3%, more preferably 0.5~1% of the whole feedstock to the reaction.

In certain embodiments, the alcoholysis reactor 110 is a continuous feed tank reactor. The preferred range of the alcoholysis reactor temperature is from 110 to 190° C., preferably from 120 to 180° C., more preferably from 130 to 170° C. The preferred pressure of the alcoholysis reactor 110 is within 5~70 kPa, preferably within 10~60 kPa, more preferably within 20~40 kPa.

In certain embodiments, the alcoholysis catalyst in the effluent from the alcoholysis reactor is recovered via a catalyst-separating device 130. In certain embodiments, the catalyst-separating device 130 is a two stage solid-liquid separator. In certain embodiments, the recovery rate of the alcoholysis catalyst is more than 99.9%, and wet content of the alcoholysis catalyst is less than 50%.

In certain embodiments, the PC-separating device comprises one, two or three vacuum distillation towers.

The preferred molar ratio of methanol to PC in the transesterification reaction is around 10:1 to around 25:1, preferably around 16:1 to around 20:1. In certain embodiments, the transesterification catalyst is NaOCH$_3$. In certain embodiments, the transesterification catalyst is present at around 0.1~2% (wt), preferably 0.3~1%, more preferably 0.5~0.8% of the whole feedstock to the reaction.

In certain embodiments, the transesterification reactor 150 is a catalytic distillation tower reactor. The preferred range of temperature for the bottom of the tower is from 75 to 95° C. The preferred range of temperature at the top of the tower is from 65 to 70° C. The preferred pressure of the catalytic distillation tower reactor is atmospheric pressure. In certain embodiments, the effluent from the top of the tower is an azeotrope comprising methanol and DMC.

Figure 2:
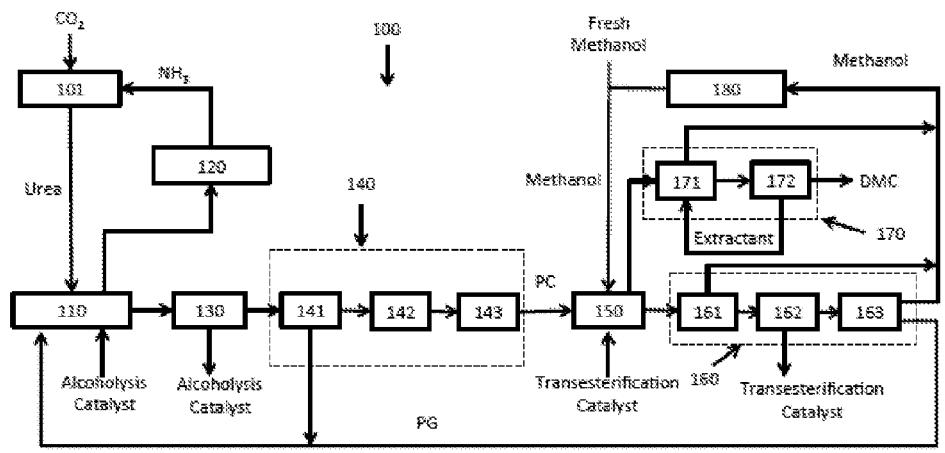
FIG. 2. A flow chart of an embodiment of the process for producing DMC.

In certain preferred embodiments, the DMC in the effluent from the top of the transesterification reactor is separated via an extractive distillation process. One such embodiment is illustrated in FIG. 2. With reference to FIG. 2, a system 100 for manufacturing DMC from CO$_2$ and methanol comprises a urea synthesis device 101, an alcoholysis reactor 110, an ammonia-purification device 120, an alcoholysis-catalyst-separating device 130, a PC-separating device 140, a transesterification reactor 150, a PG-separating device 160, a DMC-separating device 170, and a methanol-purification device 180. The PC-separating device 140 comprises a vacuum distillation tower 141, a vacuum distillation tower 142, and a vacuum distillation tower 143. The PG-separating device 160 comprises an atmospheric pressure evaporator 161, a vacuum evaporator 162, and a vacuum distillation tower 163. The DMC-separating device 170 comprises an extraction tower 171 and an extractant-regeneration tower 172.

The effluent from the bottom of the transesterification reactor 150 comprises methanol, PG and transesterification catalyst. The effluent from the bottom of the transesterification reactor 150 is first treated with the atmospheric pressure evaporator 161 to separate most of the methanol, which can be reused in the transesterification reaction. The effluent from the bottom of the atmospheric pressure evaporator 161 comprises small amount of methanol, PG and transesterification catalyst. The effluent from the bottom of the atmospheric pressure evaporator 161 can be treated with the vacuum evaporator 162 to separate the transesterification catalyst. The effluent from the vacuum evaporator 162 comprises small amount of methanol and PG. The effluent from the vacuum evaporator 162 is treated with vacuum distillation tower 163 to separate methanol and PG. The methanol separated from the vacuum distillation tower 163 can be reused in the transesterification reaction. The PG separated from the vacuum distillation tower 163 can be used in the alcoholysis reaction.

The effluent from the top of the transesterification reactor 150 is an azeotrope comprises methanol and DMC. Preferably, before feeding to the DMC-separating device 170, the azeotrope is treated with an acid resin to substantially remove the nitrogen-containing impurities. Preferably, after the treatment with the acid resin, the concentration of the nitrogen-containing impurities in the azeotrope is less than 1,000 ppm, more preferably less than 900 ppm, 800 ppm, 700 ppm, 600 ppm, 500 ppm, 400 ppm, 300 ppm, 200 ppm and 100 ppm. The azeotrope is then treated with the extraction tower 171 to separate methanol from the top of the tower and an effluent comprising DMC and extractant from the bottom of the tower.

In certain embodiments, the extractant used is ortho-xylene.

The methanol separated from the top of the extraction tower 171 can be reused in the transesterification reaction. Preferably, the methanol separated is treated with a methanol purification device 180 to remove nitrogen-containing impurities before being reused in the transesterification reaction.

The effluent from the bottom of the extraction tower 171 is treated with an extractant-regeneration tower 172 to separate the extractant and the DMC. The extractant separated can be reused in the extraction tower 171. Preferably, the extractant separated is treated with a device/reagent, e.g., an acid resin, to remove nitrogen-containing impurities before being recycled to the extraction tower 171.

The heat at the top of the extraction tower 171 can be collected and used in the transesterification reactor 150, thus minimizing energy consumption.

Figure 3:
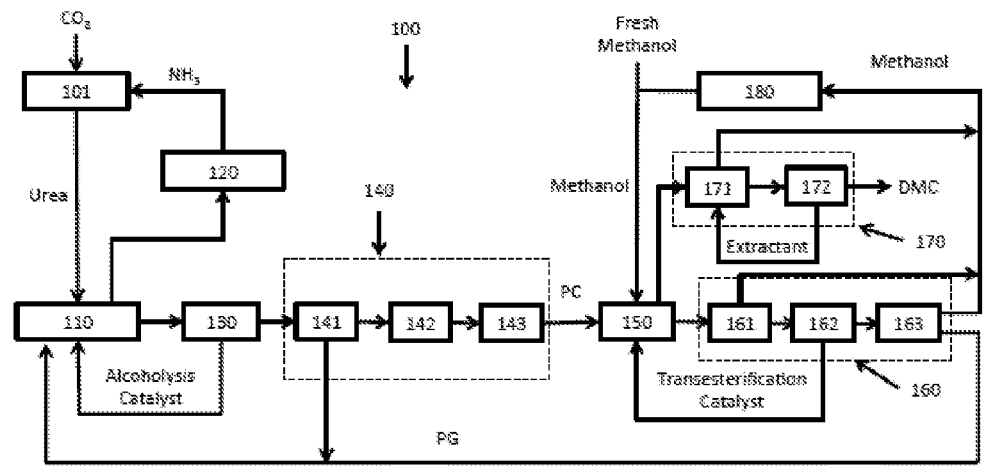
FIG. 3. A flow chart of an embodiment of the process for producing DMC.

In certain preferred embodiments, as illustrated in FIG. 3, the alcoholysis catalyst and the transesterification catalyst are recycled. With reference to FIG. 3, the alcoholysis catalyst in the effluent of the alcoholysis reactor 110 is recovered via an alcoholysis-catalyst-separating device 130 and reused in the alcoholysis reaction. The transesterification catalyst recovered from the vacuum evaporator 162 is reused in the transesterification reactor 150.

Figure 4:
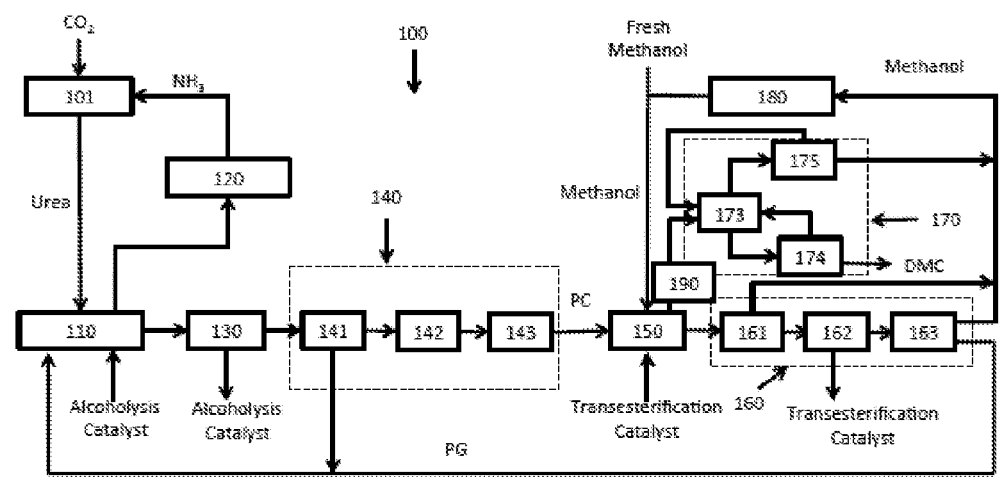
FIG. 4. A flow chart of an embodiment of the process for producing DMC.

In certain preferred embodiments, the DMC in the effluent from the top of the transesterification reactor 150 is separated via a three tower distillation unit. One such embodiment is illustrated in FIG. 4. With reference to FIG. 4, the DMC-separating device 170 comprises a pressurized tower 173, a distillation tower 174 and an atmospheric tower 175. The effluent from the top of the transesterification reactor 150 is an azeotrope comprising methanol and DMC. Before feeding to the DMC separating device 170, the azeotrope is treated with an acid resin in a nitrogen-containing-compound-treatment device 190 to substantially remove the nitrogen-containing impurities. Preferably, after the treatment of the acid resin, the concentration of the nitrogen-containing impurities in the azeotrope is less than 10 ppm, more preferably less than 9 ppm, 8 ppm, 7 ppm, 6 ppm, 5 ppm, 4 ppm, 3 ppm, 2 ppm and 1 ppm. The azeotrope is then fed to the pressurized tower 173. The effluent from the bottom of the pressurized tower 173 is fed to the distillation tower 174. The effluent from the bottom of the distillation tower 174 is DMC. The effluent from the top of the distillation tower 174 is fed back to the pressurized tower 173. The effluent from the top of the pressurized tower 173 is fed to the atmospheric tower 175. The effluent from the bottom of the atmospheric tower 175 is methanol, which is treated with the methanol-purification device 180 and reused in the transesterification reactor 150. The effluent from the top of the atmospheric tower 175 is fed back to the pressurized tower 173. The heat at the top of the pressurized tower 173 can be collected and used in the transesterification reactor 150, thus minimizing energy consumption.

The following examples are presented to illustrate the present invention. They are not intended to be limiting in any manner.

EXAMPLE 1

The following is an example of producing DMC using the process illustrated in FIG. 2.

As illustrated in FIG. 2, carbon dioxide and ammonia were fed into urea synthesis device 101 and dehydrated to produce melt urea. The melt urea so generated and PG were fed into an alcoholysis reactor 110 at molar ratio 2:1 together with an alcoholysis catalyst to produce PC and ammonia.

The alcoholysis catalyst used was a solid complex catalyst comprising at least two metal oxides, wherein the metals were selected from the group consisting of copper, zinc, magnesium, aluminum, iron, zirconium, and titanium (produced by Yashentech Corporation). The alcoholysis catalyst is present at around 0.3~1.0% (wt).

The alcoholysis reactor 110 used was a continuous feed tank reactor. The range of the alcoholysis reactor temperature was from 130 to 170° C. The pressure of the alcoholysis reactor 110 was within 20~40 kPa.

Under conditions described above, PG and urea reacted in the presence of alcoholysis catalyst to generate PC and ammonia. The ammonia generated was treated via a purification device 120 to remove impurities. Purified ammonia was used to react with CO2 in the urea synthesis device 101 to produce urea, thus forming recycled use of ammonia.

The effluent of the alcoholysis reaction 110 contained PC, PG and alcoholysis catalyst. The effluent was then treated with a catalyst-separating device 130 to separate the alcoholysis catalyst. The recovery rate of the alcoholysis catalyst is more than 99.9%, and wet content of the alcoholysis catalyst was less than 50%.

The effluent of the alcoholysis reaction was further treated with a vacuum distillation tower 141 to separate the PC and PG. The PG separated was reused in the alcoholysis reaction in the alcoholysis reactor 110.

The PC-containing effluent of the vacuum distillation tower 141 was treated with a vacuum distillation tower 142, and a vacuum distillation tower 143 to obtain PC. The PC obtained was fed to a transesterification reactor 150 to react with methanol in the presence of a transesterification catalyst. The transesterification reactor 150 was a catalytic distillation tower reactor. The molar ratio of methanol to PC in the transesterification reaction was around 10:1 to around 25:1. The transesterification catalyst was NaOCH$_3$. The transesterification catalyst was present at around 0.3~1.2% (wt). The reaction condition of the transesterification reactor 150 was as follows: atmospheric pressure; temperature for the bottom of the tower was from 75 to 95° C.; temperature at the top of the tower was from 65 to 70° C. The effluent from the bottom of the transesterification reactor 150 contained methanol, PG and transesterification catalyst; the effluent from the top of the tower was an azeotrope comprising methanol and DMC.

The effluent from the bottom of the transesterification reactor 150 was treated with the atmospheric pressure evaporator 161 to separate most of the methanol, which was treated with a methanol purification device 180 containing acid resins (DNW-I or D001). Temperature of the purification device was maintained at room temperature to 80° C. Liquid hourly space velocity (LHSV) was controlled at 0.318 5.0/h. The concentration of nitrogen-containing impurities in methanol after treatment was below 50 ppm. The methanol separated was reused together with fresh methanol in the transesterification reactor 150.

The effluent from the bottom of the atmospheric pressure evaporator 161 comprised small amount of methanol, PG and transesterification catalyst. The effluent from the bottom of the atmospheric pressure evaporator 161 was treated with vacuum evaporator 162 to separate the transesterification catalyst, which was recycled. The effluent from the vacuum evaporator 162 comprised small amount of methanol and PG. The effluent from the vacuum evaporator 162 was treated with vacuum distillation tower 163 to separate methanol and PG. The methanol separated from the vacuum distillation tower 163 was treated with the methanol purification device 180 and reused in the transesterification reaction. The PG separated from the vacuum distillation tower 163 was used in the alcoholysis reactor 110.

The effluent from the top of the transesterification reactor 150 was an azeotrope comprises methanol and DMC. The azeotrope was treated with the extraction tower 171 to separate methanol from the top of the tower and an effluent comprising DMC and extractant from the bottom of the tower. The methanol separated from the top of the extraction tower 171 was treated with the methanol purification device 180 and then reused together with fresh methanol in the transesterification reactor 150.

The effluent from the bottom of the extraction tower 171 was treated with an extractant-regeneration tower 172 to separate the extractant and the DMC. The extractant separated was reused in the extraction tower 171. The yield of DMC was over 95%.

The heat at the top of the extraction tower 171 was collected and used in the transesterification reactor 150, thus minimizing the energy consumption.

EXAMPLE 2

The following is an example of producing DMC using the process illustrated in FIG. 4.

As illustrated in FIG. 4, the whole set up of DMC manufacturing was similar as described in Example 1 with alteration to the DMC-separating device 170. In this example, the DMC-separating device 170 comprises a pressurized enrichment tower 173, a distillation tower 174 and an atmospheric tower 175. The effluent from the top of the transesterification reactor 150 is an azeotrope comprising methanol and DMC. Before feeding to the DMC separating device 170, the azeotrope was treated with a nitrogen-containing-compound-treatment device 190 containing acid resins (DNW-I or D001). Temperature of the purification device was maintained at room temperature to 80° C. Liquid hourly space velocity (LHSV) was controlled at 0.3~5.0/h. The concentration of nitrogen-containing impurities in the azeotrope after the treatment was below 10 ppm. The azeotrope was then fed to the pressurized tower 173. The effluent from the bottom of the pressurized tower 173 was fed to the distillation tower 174. The effluent from the bottom of the distillation tower 174 was DMC. The yield of DMC was above 95%.

The effluent from the top of the distillation tower 174 was fed back to the pressurized tower 173. The effluent from the top of the pressurized tower 173 was fed to the atmospheric tower 175. The effluent from the bottom of the atmospheric tower 175 was methanol, which was treated with the methanol-purification device 180 before being reused together with fresh methanol in the transesterification reactor 150. The effluent from the bottom of the atmospheric tower was fed back to the pressurized tower 173. The heat at the top of the pressurized tower 173 was collected and used in the transesterification reactor 150, thus minimizing the energy consumption.

Optionally, a nitrogen-containing-compound-treatment device was installed between the vacuum distillation tower 143 and the transesterification reactor 150, such that the concentration of nitrogen-containing impurities after treatment was less than 50 ppm.

While the invention has been particularly shown and described with reference to specific embodiments (some of which are preferred embodiments), it should be understood by those having skills in the art that various changes in form and detail may be made therein without departing from the spirit and scope of the present invention as disclosed herein.

What is claimed is:

1. A process for producing dimethyl carbonate comprising the steps of:
    (a) reacting alkylene glycol and urea in the presence of an alcoholysis catalyst to produce alkylene carbonate and ammonia;
    (b) recovering at least a portion of the alkylene carbonate produced in step (a) from an effluent from step (a);
    (c) reacting the alkylene carbonate recovered from step (b) and methanol in the presence of an transesterification catalyst to produce dimethyl carbonate and alkylene glycol;
    (d) recovering a mixture comprising the dimethyl carbonate and unreacted methanol; and
    (e) separating the dimethyl carbonate from the mixture, wherein nitrogen-containing impurities are substantially removed in one or more steps of the process such that the mixture in separation step (e) is substantially free of nitrogen-containing impurities.

2. The process of claim 1, wherein the nitrogen-containing impurities are substantially removed from the alkylene carbonate in recovery step (b).

3. The process of claim 1, wherein the nitrogen-containing impurities are substantially removed from the mixture in reaction step (c).

4. The process of claim 1, wherein the first portion of unreacted methanol is separated from the mixture and reused in step (c).

5. The process of claim 4, wherein the nitrogen-containing impurities are substantially removed from the first portion of unreacted methanol separated.

6. The process of claim 4, wherein the first portion of unreacted methanol is separated via a pressure varying azeotrope separation process.

7. The process of claim 4, wherein the first portion of unreacted methanol is separated via an extraction process.

8. The process of claim 7, wherein the extractant used in the extraction process is ortho-xylene.

9. The process of claim 1, wherein the nitrogen-containing impurities are substantially removed via an acid resin.

10. The process of claim 1, wherein at least a portion of the ammonia produced in reaction step (a) is recovered to react with $CO_2$ to produce urea.

11. The process of claim 10, wherein the ammonia recovered is further purified to remove substantially all organic impurities before reacting with $CO_2$ to produce urea.

12. The process of claim 1, wherein at least a portion of the alcoholysis catalyst is recovered from the effluent from step (a) and reused in step (a).

13. The process of claim 1, wherein unreacted alkylene glycol is recovered from the effluent from step (a) and reused in step (a).

14. The process of claim 1, wherein unreacted methanol is recovered from an effluent from step (c) and reused in step (c).

15. The process of claim 1, wherein at least a portion of the transesterification catalyst is recovered from an effluent from step (c) and reused in step (c).

16. The process of claim 1, wherein the alkylene glycol is ethylene glycol or propylene glycol.

17. The process of claim 1, wherein the alcoholysis catalyst comprises at least two metal oxides, wherein the metals are selected from the group consisting of copper, zinc, magnesium, aluminum, iron, zirconium, and titanium.

18. The process of claim 1, wherein the alkylene glycol produced in reaction step (c) is recovered and reused in reaction step (a).

19. The process of claim 1, wherein conversion percentage of urea is in the range of 95~100%.

20. The process of claim 1, wherein conversion percentage of alkylene carbonate is in the range of 95~100%.

* * * * *